United States Patent [19]

Biere et al.

[11] 3,956,295
[45] May 11, 1976

[54] CARBAZOLE DERIVATIVES
[75] Inventors: Helmut Biere; Hanns Ahrens; Clemens Rufer; Eberhard Schroder; Henning Koch, all of Berlin, Germany
[73] Assignee: Schering Aktiengesellschaft, Berlin & Bergkamen, Germany
[22] Filed: July 17, 1974
[21] Appl. No.: 489,162

[30] Foreign Application Priority Data
July 18, 1973 Germany............................ 2337154

[52] U.S. Cl. .................. 260/247.5 FP; 260/308 D; 260/315; 424/248; 424/269; 424/274
[51] Int. Cl.² ......................................... C07D 209/82
[58] Field of Search ........ 260/315, 308 D, 247.5 FP

[56] References Cited
UNITED STATES PATENTS
3,674,875 7/1972 Shen et al. ...................... 260/315
3,896,145 7/1975 Berger et al. ...................... 260/315

OTHER PUBLICATIONS
J. Heterocyclic Chem. 7:239–241 (1970) Allen.
J. Chem. Soc. Pt. C. (1969) 1518–1520, Joshi et al.
Tetrahedron Letters (1968) 2744, Miwa et al.
Tetrahedron 21:681–685 (1965) Chakraborty et al.
Chemical Abstracts 58:11,314 d (1963) Julia et al.
Chemical Abstracts 59:8685 c, d (1963) Dokunikhin.
Jacs, 84:94–97 (1962) Wenkert et al.

*Primary Examiner*—Sherman D. Winters
*Attorney, Agent, or Firm*—Millen, Raptes & White

[57] ABSTRACT
Carbazoles of the formula

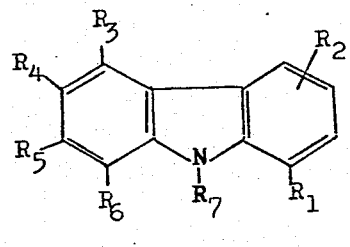

wherein $R_1$ is hydroxymethyl, alkanoyloxymethyl, tetrazolyl, cyano, oximinocarbonyl, aminocarbonyl, carboxyl and salts thereof with physiologically acceptable bases and the esters thereof with physiologically acceptable alcohols and amides thereof with physiologically acceptable amines, $R_2$ through $R_6$ each are a hydrogen atom, halogen atom, lower alkyl, trifluoromethyl, or lower alkoxy, or $R_5$ and $R_6$ collectively are a five- or six-membered isocyclic ring, and $R_7$ is a hydrocarbon of 3–8 carbon atoms or, when at least one of the $R_2$ through $R_6$ is other than a hydrogen atom, a hydrogen atom, methyl or ethyl, and the corresponding compounds wherein $R_7$ is a hydrogen atom, methyl or ethyl, and the 5,6,7,8-tetrahydrocarbazoles, possess topical anti-inflammatory activity.

49 Claims, No Drawings

CARBAZOLE DERIVATIVES

BACKGROUND OF THE INVENTION

This invention relates to novel carbazoles. 5.6.7.8-Tetrahydrocarbazole-1-carboxylic acid and carbazole-1-carboxylic acid are known (J. chem. Soc., London, 1945, 530).

SUMMARY OF THE INVENTION

In a composition aspect, this invention relates to novel carbazoles of the general Formula I

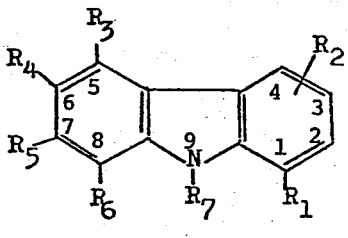

wherein R is hydroxymethyl, alkanoyloxymethyl, tetrazolyl, cyano, oximinocarbonyl, aminocarbonyl, carboxyl and salts thereof with physiologically acceptable bases and the esters thereof with physiologically acceptable alcohols and amides thereof with physiologically acceptable amines, $R_2$ through $R_6$ each are a hydrogen atom, halogen atom, lower alkyl, trifluoromethyl or lower alkoxy, or $R_5$ and $R_6$ collectively are a five- or six-membered isocyclic ring, and $R_7$ is hydrocarbon of 3-8 carbon atoms or, when at least one of the $R_2$ through $R_6$ is other than a hydrogen atom, methyl, ethyl or a hydrogen atom.

The novel carbazole derivatives are pharmacologically active compounds and possess marked anti-inflammatory activity topically.

In another composition aspect, this invention relates to pharmaceutical compositions comprising a compound of Formula I wherein R, has the values given for those compounds, excepting oximinocarbonyl, $R_2$ through $R_6$ have the values given for those compounds and $R_7$ in every instance is a hydrogen atom or hydrocarbon of 1–8 carbon atoms, in admixture with a pharmaceutically acceptable carrier.

In a method of use aspect, this invention relates to the method of treatment of topical inflammatory conditions which comprises administering topically an effective amount of a pharmaceutical composition of this invention.

In a process aspect, this invention relates to processes for the production of the compounds of this invention.

In a further composition aspect, this invention relates to novel 5, 6, 7, 8-tetrahydrocarbazoles of Formula II wherein $R_1$ through $R_7$ have the values given the Formula I.

In still a further composition aspect, this invention relates to pharmaceutical compositions comprising a compound of Formula III wherein $R_1$ through $R_7$ have the values given above for the active compounds of Formula I of pharmaceutical compositions of this invention.

DETAILED DISCUSSION

As will be explained in greater detail below, the novel carbazole derivatives of this invention are distinguished by their greater topical anti-inflammatory effectiveness compared to the known N-phenylanthranilic acid derivatives of similar structure which possess only a very minor topical anti-inflammatory activity.

As demonstrated by the results of pharmacological tests set out below, the novel carbazole derivatives can have differing $R_1$ through $R_7$ substituents without losing their topical anti-inflammatory effectiveness.

Examples of $R_1$ groups are, in addition to hydroxymethyl, tetrazolyl, cyano, oximinocarbonyl and aminocarbonyl and particularly carboxyl and the salts thereof with physiological bases and the esters thereof with physiologically acceptable alcohols and the amides thereof with physiologically acceptable amines. Examples of physiologically compatible salts of the carboxyl group $R_1$ are the alkali or alkaline earth metal salts, e.g., the sodium salt or the calcium salt.

Physiologically acceptable alcohols with which the carboxyl group can be esterified are, for example, straight-chain or branched or cyclic, saturated or unsaturated hydrocarbon, which can optionally be interrupted by an oxygen atom or a nitrogen atom, or which can be substituted with one or more of hydroxy, amino, carboxyl, e.g., alkanols, alkenols, alkinols, cycloalkanols, cycloalkenols, cycloalkyl-alkanols, phenylalkanols, phenyl-alkenols, alkanediols, hydroxycarboxylic acids, amino-alkanols, or alkylamino alkanols, and dialkylamino-alkanols wherein each alkyl is of 1–4 carbon atoms.

Specific examples of alcohols suitable for the esterification of the carboxyl group in the 1-position are methyl, carboxymethyl, ethyl, 2-hydroxyethyl, 2-methoxyethyl, 2-amino-ethyl, 2-dimethylaminoethyl, 2-carboxyethyl, propyl, allyl, cyclopropylmethyl, isopropyl, 3-hydroxypropyl, propinyl, 3-aminopropyl, butyl, sec.-butyl, tert.-butyl, 2-butyl, cyclobutyl, pentyl, isopentyl, tert.-pentyl, 2-methylbutyl, cyclopentyl, hexyl, cyclohexyl, cyclohex-2-enyl, cyclopentylmethyl, heptyl, benzyl, 2-phenylethyl, octyl, bornyl, isobornyl, menthyl, nonyl, decyl, 3-phenylpropyl, 3-phenylprop-2-entyl, undecyl and dodecyl alcohols.

Preferred physiologically compatible amines with which the carboxyl group in the 1-position can be amidated are alkylamines, dialkylamines, alkanolamines, dialkanolamines of 1–6 carbon atoms in the alkyl or alkanol group, or five- or six-membered N-heterocyclic amines, e.g., methylamine, ethylamine, isopropylamine, ethanolamine, dimethylamine, diethylamine, diethanolamine, pyrrolidine, piperidine, morpholine, or N-methylpiperazine.

$R_1$ can also be an alkanoyloxy-methyl group, preferably those wherein the alkanoyl group is of 1–8 carbon atoms, e.g., formyloxy-, acetyloxy-, propionyloxy-, butyryloxy- and hexanoyloxy-methyl.

Preferred $R_2$ through $R_6$ lower alkyl groups are those of 1–4 carbon atoms, e.g., methyl, ethyl, propyl, isopropyl, butyl and tert.-butyl.

$R_2$ through $R_6$ halogen atoms are preferably fluorine, chlorine or bromine.

The five- and six-membered isocyclic rings formed collectively by $R_5$ and $R_6$ with the ring carbon atoms to which they are attached are the carbocyclic rings cyclopentene, cyclohexene and benzene.

Examples of $R_7$ hydrocarbon groups containing 1–8 carbon atoms are straight-chain or branched alkyl, optionally substituted by three- to six-membered cycloalkyl groups or by phenyl groups, e.g., methyl, ethyl, propyl, isopropyl, butyl, hexyl, 3-cyclopropylpropyl, cyclopentylmethyl and benzyl.

$R_2$ can be in the 3- or 4-position.

Preferred classes of compounds of this invention are those wherein:

a. $R_1$ is —COOH; and the alkali salts thereof
b. $R_1$ is —CONH$_2$;
c. $R_1$ is —COO alkyl of 1 to 8 carbon atoms in the alkyl group
d. $R_2$, $R_4$ and preferably also $R_3$ each are hydrogen atoms, especially those of (a), (b) and (c);
e. $R_5$ and $R_6$ are alike or different and are other than a hydrogen atom, preferably Cl or CH$_3$, particularly those wherein $R_5$ is Cl and $R_6$ is CH$_3$ and especially those of (a), (b), (c) and (d);
f. $R_7$ is H or CH$_3$, especially those of (a), (b), (c), (d) and (e).

In addition to the compounds specifically named herein after, other compounds of this invention are 7.8-tetramethylene,carbazole-1-carboxylic acid and
7.8-trimethylene-carbazole-1-carboxylic acid.

In its process aspect, this invention relates to a process for the production of the novel carbazole derivatives of general Formula I, which comprises dehydrogenating in a conventional manner a tetrahydrocarbazole derivative of the general Formula II or III

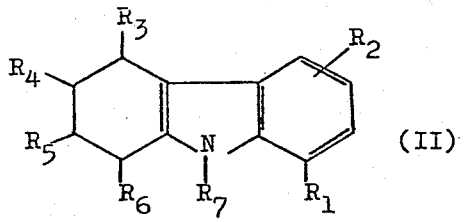

(II)

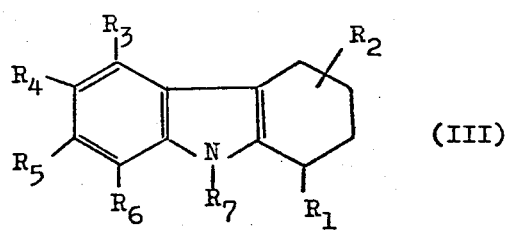

(III)

wherein $R_1$ through $R_7$ have the values given for Formula I, and optionally a secondary amino group present in the 9-position is alkylated; a free hydroxy group is esterified or etherified; an ester group is saponified; and a free carboxyl group or reactive derivative thereof is converted into a salt, ester, amide, cyano group, oximinocarbonyl group, hydroxymethyl group or tetrazolyl group.

The dehydrogenation of the tetrahydrocarbazole derivatives of general Formulae II and III is conducted according to conventional methods. Thus, it is possible, for example, to dehydrogenate compounds of Formulae II or III with noble metal catalysts of the platinum group, e.g., platinum oxide catalysts and especially also palladium-carbon catalysts.

The reaction is conducted preferably in a high-boiling aromatic solvent, e.g., toluene, xylene, cumene, anisole, chlorobenzene, dichlorobenzene, or chlorotoluene. The reaction temperature is concomitantly determined by the choice of solvent and is usually about 100°–200° C., preferably 130°–180° C. If the tetrahydrocarbazole derivatives of general Formulae II or III contain a halogen atom, it can be split off, if a halogen-free solvent is employed for the reaction. If the reaction is effected in a halogen-containing solvent (which contains the same halogen atom as the compound to be dehydrogenated), it is possible to avoid the splitting off of halogen atoms.

Additional suitable oxidizing agents for the process are quinones, e.g., p-benzoquinone, chloranil, tetrachloro-o-benzo-quinone, dichlorodicyanobenzoquinone, and inorganic oxidizing agents, e.g., lead dioxide, manganese dioxide and sulfur. Suitable solvents are high-boiling solvents such as xylene, cumene, chlorobenzene, dichlorobenzene, etc. The reaction temperature is usually 100°–200° C., preferably 130°–160°C.

The optional subsequent alkylation of a secondary amino group present in the 9-position is likewise accomplished according to the conventional methods customarily utilized for the N-alkylation of indole derivatives.

Thus, it is possible, for example, to metallize the nitrogen atom of the carbazole ring by reaction with a metal hydride or metal amide, e.g., sodium hydride or sodium amide, and to treat thee thus-obtained reactive compounds with a halogenide (chloride, bromide, or iodide) of the lastly desired hydrocarbon group. For this reaction, which is conducted at a reaction temperature of about 0° C. to 120° C., polar aprotic solvents are preferably employed, e.g., dimethylformamide, N-methylpyrrolidone, or hexamethylphosphoric triamide.

The esterification of the free hydroxymethyl group, following as an optional measure, is likewise achieved according to conventional modes of operation. An example of a possible esterification method is the esterification of a hydroxy compound with an acid anhydride or acid chloride in the presence of an aromatic N-heterocycle, e.g., pyridine, collidine, or lutidine, or in the presence of an aqueous solution of a basic alkali metal compound, e.g., sodium bicarbonate, potassium bicarbonate, sodium carbonate, sodium hydroxide, or potassium hydroxide.

The optional subsequent saponification of the esters takes place according to known methods, e.g., saponification of the esters in water or aqueous alcohol in the presence of an acidic catalyst, e.g., hydrochloric acid, sulfuric acid, p-toluenesulfonic acid, or in the presence of a basic catalyst, e.g., potassium bicarbonate, potassium carbonate, sodium hydroxide or potassium hydroxide.

The optional subsequent esterification of the free acids is likewise accomplished in accordance with conventional operating methods, for example, with diazomethane or diazoethane, thus obtaining the corresponding methyl or ethyl ester. A generally applicable method is the reaction of an acid with an alcohol in the presence of carbonyl diimidazole or dicyclohexylcarbodiimide.

It is also possible, for example, to react the free acid in the presence of copper (I) oxide or silver oxide with an alkyl halogenide.

A further method is the conversion of a free acid with the corresponding dimethylformamide alkyl acetal into the corresponding acid alkyl ester. The acids can be reacted in the presence of a strongly acidic catalyst, e.g., hydrogen chloride, sulfuric acid, perchloric acid, trifluoromethyl-sulfonic acid or p-toluenesulfonic acid, with an alcohol or a lower alkanecarboxylic acid ester of an alcohol.

It is also possible to convert the carboxylic acids into the acid chlorides or mixed acid anhydrides and to react these functionally reactive derivatives in the presence of a basic catalyst, e.g., pyridine, collidine, lutidine, or 4-dimethylaminopyridine, with an alcohol.

The carboxylic acid salts are produced, for example, during the saponification of the esters with a basic catalyst or during the neutralization of the acids with an alkali carbonate or alkali hydroxide, e.g., sodium carbonate, sodium bicarbonate, sodium hydroxide, potassium carbonate, potassium bicarbonate or potassium hydroxide.

It is also possible to react esters of general Formula I with the finally desired alcohol in the presence of an acidic or basic catalyst. In this process, preferred acidic or basic catalysts are hydrogen chloride, sulfuric acid, phosphoric acid, p-toluenesulfonic acid, trifluoroacetic acid, e.g., alkali, alkaline earth and aluminum alcoholates.

The subsequent amide formation or hydroxamic acid formation from the free carboxylic acids or the reactive derivatives thereof is likewise conducted according to methods known for this purpose. For example, the carboxylic acids can be reacted under conventional conditions with an amine or a hydroxylamine in the presence of dicyclohexylcarbodiimide, thus obtaining the corresponding aminocarbonyl compounds.

It is also possible to convert the acid chlorides, mixed anhydrides, or esters corresponding to the carboxylic acids into the corresponding amines or hydroxamic acids under the know conditions by treatment with ammonia, with an amine, or with hydroxylamine.

The optional subsequent conversion of reactive carboxylic acid derivatives into nitriles, is likewise accomplished according to the known methods, e.g., by treating the corresponding aminocarbonyl compounds, under the conventional conditions, with a dehydrating agent, e.g., dicyclohexylcarbodiimide, carbonyl diimidazole, polyphosphoric acid, thionyl chloride, or phosphorus oxychloride.

In order to produce the corresponding hydroxymethyl compounds from reactive derivatives of carboxylic acids, known methods are likewise employed. Thus, the carboxylic acid esters can be reduced to the corresponding hydroxymethyl compounds, for example, in an aprotic, halogen-free solvent, e.g., in an ether, for example, diethyl ether, diisopropyl ether, tetrahydrofuran or glycol dimethyl ether, with a complex metal hydride, e.g., lithium aluminum hydride diisobutyl aluminum hydride or dethyl aluminum hydride.

To produce the compounds of Formula I wherein $R_1$ is tetrazolyl, conventional methods can also be employed. Thus, the nitriles can be reacted, for example, to the corresponding tetrazolyl compounds in a polar aprotic solvent, e.g., dimethylformamide, N-methylacetamide, N-methylpyrrolidone, or hexamethylphosphoric triamide, under the conventional conditions with an alkali azide, e.g., sodium azide.

The topical antiphlogistic activity of the novel carbazole derivatives can be determined according to the Tonelli method, as follows:

The compound to be tested is dissolved in an irritant, consisting of 4 parts of pyridine, 1 part of distilled water, 5 parts of ether, and 10 parts of a 4% ether - croton oil solution. With this test solution, felt strips are saturated, which strips were attached to the inner sides of a microscope slide tweezer. Under slight pressure, these felt strips are pressed for 15 seconds against the right ear of male rates weighing 100–600 g. The left ear remains untreated and serves as comparison. Three hours after application, the animals are sacrificed and 9 mm. large disks are punched out of their ears. The weight difference between the disk of the right ear and that of the left ear is a measure for the thus-formed edema.

Control animals are treated in the same manner, except the irritant solution utilized does not contain a test compound.

The anti-inflammatory effectiveness is determined by dividing the average difference of the ear weights of the treated group by the average difference of the ear weights of the control group.

The following table shows the effectiveness of the carbazole derivatives as compared to the known antiphlogistically active compounds I and II

TABLE

| No. | Compound | Concentration mg./ml. | Antiphlogistic Activity in % |
|---|---|---|---|
| I | N-(3-Trifluoromethylphenyl)-anthranilic acid | 3.75 | 0 % |
| | | 7.5 | 0 % |
| | | 15.0 | 20 % |
| II | Hydrocortisone acetate | 7.5 | 19 % |
| | | 15.0 | 41 % |
| III | 9-Methylcarbazole-1-carboxylic acid | 7.5 | 33 % |
| IV | 6-Fluorocarbazole-1-carboxylic acid | 7.5 | 24 % |
| | | 15.0 | 41 % |
| V | 7-Trifluoromethylcarbazole-1-carboxylic acid | 7.5 | 40 % |
| | | 15.0 | 56 % |
| VI | 7,8-Dichlorocarbazole-1-carboxylic acid (2'-dimethylaminoethyl) ester | 7.5 | 37 % |
| | | 15.0 | 40 % |
| VII | 7-Chloro-8-methylcarbazole-1-carboxylic acid | 3.75 | 42 % |
| | | 7.5 | 59 % |
| | | 15.0 | 85 % |
| VIII | 5-Chloro-8-methylcarbazole-1-carboxylic acid | 7.5 | 26 % |
| | | 15.0 | 52 % |
| IX | 8-Chloro-7-methylcarbazole-1-carboxylic acid | 3.75 | 38 % |
| | | 7.5 | 62 % |
| | | 15.0 | 83 % |
| X | 7-Chloro-3,8-dimethylcarbazole-1-carboxylic acid | 7.5 | 2 % |
| | | 15.0 | 56 % |
| XI | 7-Chloro-8,9-dimethylcarbazole-1-carboxylic acid | 7.5 | 46 % |
| | | 15.0 | 69 % |
| XII | 7-Chloro-8-methylcarbazole-1-carboxylic acid amide | 7.5 | 31 % |
| | | 15.0 | 54 % |
| XIII | 7-Chloro-8-methylcarbazole-1-carbohydroxamic acid | 3.75 | 28 % |
| | | 7.5 | 50 % |
| | | 15.0 | 70 % |
| XIV | 7-Chloro-1-hydroxymethyl-8-methylcarbazole | 7.5 | 36 % |
| | | 15.0 | 41 % |
| XV | 7,8-Dimethylcarbazole-1-carboxylic acid morpholide | 7.5 | 36 % |
| XVI | Benzo[a]carbazole-1-carboxylic acid | 3.75 | 22 % |
| | | 7.5 | 46 % |
| XVII | Carbazole-1-carboxylic acid | 7.5 | 40 % |
| | | 15.0 | 50 % |

It can be seen from the table that the novel carbazole derivatives (III - XVII) compared to the known N-phenylanthranilic acid derivatives of analogous structure (I) superior anti-inflammatory activity. The anti-inflammatory activity of the novel carbazole derivatives is, upon local application, approximately as strong as that of conventional, anti-inflammatory corticoids.

Surprisingly, not only the novel carbazole derivatives of this invention, but the known carbazole derivatives differing from those of Formula I in that the substituents $R_2$ through $R_7$ therein are all hydrogen atoms, possess a pronounced topical anti-inflammatory effectiveness, as can be seen from the table. Thus, these compounds also are suitable as the active agent for the novel pharmaceutical compositions having topical anti-inflammatory activity and the use thereof to heat topical inflammatory conditions.

The corticoids heretofore utilized for the treatment of skin inflammations in addition to the topical effect, also posses systemic corticoid activity. These corticoids can, even with topical administration, enter the blood stream by resorption through the inflammed skin or because of skin injuries, where they affect, as hormonally-active compounds, the body functions in a great variety of ways.

This disadvantage does not exist in the topically active carbazole derivatives of the present invention.

Moreover, the carbazole derivatives of this invention have the advantages that they have a low toxicity and they exert a certain antibacterial and antifungal effectiveness which is definitely desirable in the topical treatment of topical inflammations.

The carbazoles of this invention are suitable, in combination with the vehicles customary in galenic pharmacy, for the local treatment of allergies, contact dermatitis, eczemas of a great variety of types, neurodermatitis, erythrodermia, burns, pruritus vulvae et ani, rosacea, erythematodes cutaneus, psoriasis, lichen ruber planus et verrucosus, and similar skin diseases.

The production of the special drug preparations is effected in the usual manner by converting one or a mixture of the carbazole derivatives, together with suitable additives, into the desired forms of application, e.g., solutions, lotions, ointments, creams, inhalants, or plasters. In the thus-formulated medicinal agents, the concentration of effective agent is dependent on the form of application. In case of lotions and ointments, an active agent concentration of 0.005 to 5% is preferably utilized.

The starting compounds for the process of this invention are known, or they can be readily prepared in a simple manner in accordance with the following formula scheme:

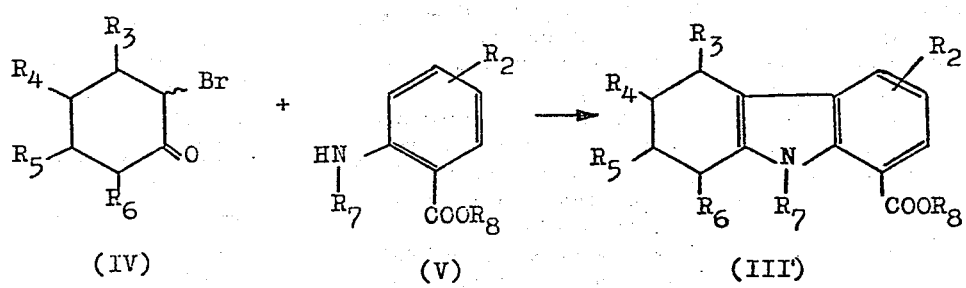

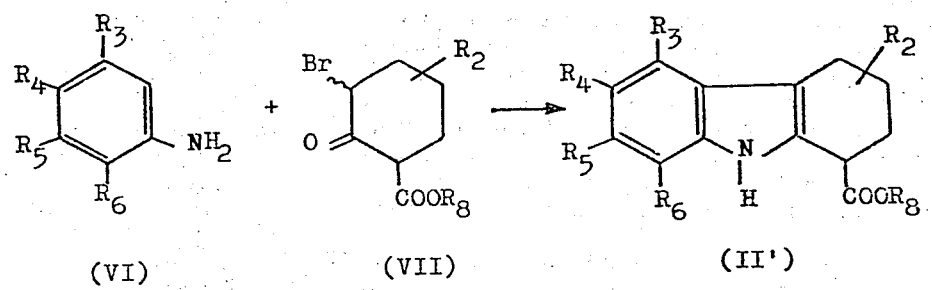

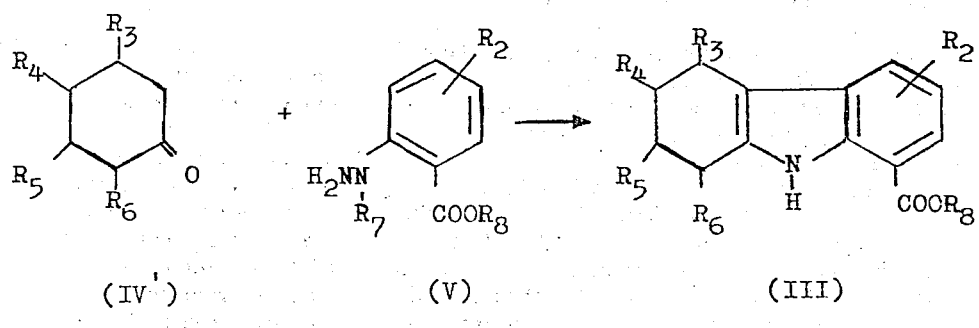

wherein
R$_2$ through R$_7$ have the values given above and
R$_8$ is lower alkyl.

The reaction is accomplished by heating the components, for example under an inert gas atmosphere, in the presence of Lewis acids, such as zinc chloride, and optionally with the addition of a lower alcohol, such as ethanol, or a lower carboxylic acid, such as acetic acid, as the solvent, to 50°–200°C.

In the thus-obtained esters, it is possible under the conditions describes above optionally to alkylate a secondary amino group present in the 9-position; to esterify or etherify free hydroxyl groups; to saponify ester groups; and to convert free carboxyl groups or reactive derivatives thereof into salts, esters, amides, oximinocarbonyl groups, cyano groups, hydroxymethyl groups, or tetrazolyl groups.

Basically, this condensation can also be conducted with the use of other α-halocyclohexanone derivatives, such as, for example, α-chloro- or α-iodocyclohexanone derivatives. Furthermore, it is possible to effect the reaction without the use of Lewis acids or to use other catalysts, such as boron trifluoride, phosphoric acid, hydrogen chloride.

If the reaction is conducted with the use of substituted anilines, the substituted aniline is advantageously employed in an excess, preferably with a 2.2- to 2.5-molar excess. The reaction can be accomplished with or without a solvent. Preferred solvents are alcohols, such as ethanol and butanol, or ethers, such as dioxane, dimethoxyethane, etc. hen conducting the procedure without a solvent, the excess of the aniline component can serve as the solvent. In both cases, a catalyst can be added, such as zinc chloride, for example.

The reaction is preferably conducted under a protective gas atmosphere, e.g. nitrogen or a noble gas.

The reaction temperature is also determinend by the choice of solvent and usually is 80°–200°C.; preferably, the temperature is 140°–150°C., especially when operating without a solvent or when using solid aniline components.

The reaction takes place under normal or reduced pressures, preferably at 100 mm. Hg.

If substituted phenylhydrazines are used as the starting compounds (IV), the reaction takes placed preferably at temperatures of between 50° and 150°C. and can be accomplished with or without solvents, using the catalysts known from the Fischer indole synthesis, such as for example, zinc chloride, hydrogen chloride, sulfuric acid, phosphoric acid, polyphosphoric acid, boron trifluoride, etc. Preferred solvents are acetic acid, glacial acetic acid, and alcohols. However, it is also prossible to conduct the reaction without solvents in molten zinc chloride or in polyphosphoric acid and phosphoric acid.

The heretofore unknown compounds of general Formula II and 5, 6, 7, 8-tetrahydrocarbazole-1-carboxylic acid itself, as well as the esters and amides thereof, are surprisingly also distinguished by a pronounced anti-inflammatory activity upon local application and can be used as active medicinal agents in the same manner as the carbazole derivatives.

Therefore, the present invention also relates to the novel 5, 6, 7, 8-tetrahydrocarbazole-1-carboxylic acid derivatives, the preparation thereof, and the use thereof.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1 a. 10 g. of the ethyl ester of 3-bromo-2-oxocyclohexanecarboxylic acid is mixed with 10 g. of 3-methoxyaniline and heated under a slight vacuum (about 100 torr [mm. Hg]) and agitation for 7 hours to 140° C.

After cooling, the mixture is diluted with carbon tetrachloride, filtered, the organic phase is washed, concentrated under vacuum, and the residue purified by chromatography on silica gel by means of cyclohexane-benzene as the eluent, thus obtaining the ethyl ester of 6-methoxy-1,2,3,4-tetrahydrocarbazole-1-carboxylic acid.

b. 2.05 g. of the ethyl ester of 6-methoxy-1,2,3,4-tetrahydrocarbazole-1-carboxylic acid is dissolved in 20 ml. of xylene, mixed with 2 g. of 10% palladium-carbon catalyst, and refluxed for 4 hours. After the reaction mixture has cooled, the catalyst is filtered off, the solution is concentrated under vacuum, the residue is recrystallized from benzene, and 1.5 g. of the ethyl ester of 6-methoxycarbazole-1-carboxylic acid is thus produced, m.p. 107° C.

EXAMPLE 2 a. Under the conditions of Example 1(a), 10 g. of 3-bromo-2-oxocyclohexanecarboxylic acid ethyl ester is reacted with 2-methoxyaniline to the ethyl ester of 8-methoxy-1,2,3,4-tetrahydrocarbazole-1-carboxylic acid.

b. The ethyl ester of 8-methoxy-1,2,3,4-tetrahydrocarbazole-1-carboxylic acid is dissolved in chlorobenzene and, after adding 10% palladium-carbon, dehydrogenated as described in Example 1(b). After recrystallization from ethanol, the ethyl ester of 3-methoxycarbazole-1-carboxylic acid is obtained in a 73% yield, m.p. 76° C.

EXAMPLE 3 a. Under the conditions of Example 1(a), 10 g. of the ethyl ester of 3-bromo-2-oxocyclohexanecarboxylic acid is reacted with 2-methylaniline to the ethyl ester of 8-methyl-1,2,3,4-tetrahydrocarbazole-1-carboxylic acid.

b. The ethyl ester of 8-methyl-1,2,3,4-tetrahydrocarbazole-1-carboxylic acid is dissolved in cumene and, after adding 10% palladium-carbon, dehydrogenated as set forth in Example 1(b). After recrystallization from methanol, the ethyl ester of 8-methylcarbazole-1-carboxylic acid is obtained in a 75% yield, m.p. 68° C.

EXAMPLE 4 a. Under the conditions of Example 1(a), 10 g. of the ethyl ester of 3-bromo-2-oxocyclohexanecarboxylic acid is reacted with 3-fluoroaniline to the ethyl ester of 7-fluoro-1,2,3,4-tetrahydrocarbazole-1-carboxylic acid.

b. The thus-produced tetrahydrocarbazole derivative is dissolved in chlorobenzene, combined with 10% palladium-carbon, and dehydrogenated as described in Example 1(b), thus obtaining after recrystallization from isopropyl alcohol the ethyl ester of 7-fluorocarbazole-1-carboxylic acid in a 77% yield, m.p. 132° C.

EXAMPLE 5 a. Under the conditions of Example 1(a), 10 g. of the ethyl ester of 3-bromo-2-oxocyclohexanecarboxylic acid is reacted with 4-fluoroaniline to the ethyl ester of 6-fluoro-1,2,3,4-tetrahydrocarbazole-1-carboxylic acid.

b. The thus-produced tetrahydrocarbazole derivative is dissolved in o-dichlorobenzene, combined with 10% palladium-carbon, and dehydrogenated as described in Example 1(b), thus obtaining after recrystallization from isopropyl alcohol, the ethyl ester of 6-fluorocarbazole-1-carboxylic acid in a 60% yield, m.p. 130° C.

EXAMPLE 6 a. Under the conditions as described in Example 1(a), 10 g. of the ethyl ester of 3-bromo-2-oxocyclohexanecarboxylic acid is reacted with 3-trifluoromethylaniline to obtain the ethyl ester of 7-trifluoromethyl-1,2,3,4-tetrahydrocarbazole-1-carboxylic acid.

b. The thus-produced tetrahydrocarbazole derivative is dissolved in o-dichlorobenzene, combined with 10% palladium-carbon, and dehydrogenated as in Example 1(b), thus obtaining after recrystallization from isopropyl alcohol the ethyl ester of 7-trifluoromethylcarbazole-1-carboxylic acid in a 55% yield, m.p. 80° C.

EXAMPLE 7 a. Under the reaction conditions of Example 1(a), but with the addition of 0.5 g. of zinc chloride after 2 hours, 10 g. of the ethyl ester of 3-bromo-2-oxocyclohexanecarboxylic acid is reacted with 5-chloro-2-methylaniline to the ethyl ester of 5-chloro-8-methyl-1,2,3,4-tetrahydrocarbazole-1-carboxylic acid.

b. The thus-produced tetrahydrocarbazole derivative is dissolved in chlorobenzene, combined with 10% palladium-carbon, and dehydrogenated as set forth in Example 1(b), thus obtaining, after recrystallization from isopropyl alcohol - methanol, the ethyl ester of 5-chloro-8-methylcarbazole-1-carboxylic acid in an 85% yield, m.p. 102° C.

EXAMPLE 8 a. Under the conditions of Example 7(a), 10 g. of the ethyl ester of 3-bromo-2-oxocyclohexanecarboxylic acid is reacted with 3-chloro-2-methylaniline to the ethyl ester of 7-chloro-8-methyl-1,2,3,4-tetrahydrocarbazole-1-carboxylic acid.

b. The thus-produced tetrahydrocarbazole derivative is dissolved in chlorobenzene, mixed with 10% palladium-carbon, and dehydrogenated as described in Example 1(b), thus obtaining, after recrystallization from isopropyl alcohol - methanol, the ethyl ester of 7-chloro-8-methylcarbazole-1-carboxylic acid in a 70% yield, m.p. 98° C.

EXAMPLE 9

600 mg. of the ethyl ester of 7-chloro-8-methyl-1,2,3,4-tetrahydrocarbazole-1-carboxylic acid is combined with 1 g. of chloranil and 15 ml. of xylene and refluxed for 25 hours. The solvent is then distilled off, the residue is combined with sodium dithionite and dilute sodium hydroxide solution, and extracted repeatedly with benzene. The organic phase is washed, concentrated, the residue recrystallized from isopropyl alcohol - methanol, and the thus-obtained product is 350 mg. (= 61%) of the ethyl ester of 7-chloro-8-methylcarbazole-1-carboxylic acid, m.p. 97° C.

EXAMPLE 10 a. Under the conditions of Example 7(a), 10 g. of the ethyl ester of 3-bromo-2-oxocyclohexanecarboxylic acid is reacted with 5-chloro-2-methoxyaniline to the ethyl ester of 5-chloro-8-methoxy-1,2,3,4-tetrahydrocarbazole-1-carboxylic acid.

b. The thus-produced tetrahydrocarbazole derivative is dissolved in chlorobenzene, mixed with 10% palladium-carbon, and dehydrogenated as described in Example 1(b), thus obtaining after recrystallization from isopropyl alcohol, in a 52% yield, the ethyl ester of 5-chloro-8-methoxycarbazole-1-carboxylic acid, m.p. 113° C.

EXAMPLE 11 a. Under the conditions set forth in Example 7(a), 10 g. of the ethyl ester of 3-bromo-2-oxo-5-methylcyclohexanecarboxylic acid is reacted with 3-chloro-2-methylaniline to the ethyl ester of 7-chloro-3,8-dimethyl-1,2,3,4-tetrahydrocarbazole-1-carboxylic acid.

b. The thus-produced tetrahydrocarbazole derivative is dissolved in chlorobenzene, combined with 10% palladium-carbon, and dehydrogenated as described in Example 1(b). After recrystallization from isopropyl alcohol, the ethyl ester of 7-chloro-3,8-dimethylcarbazole-1-carboxylic acid is obtained in a 70% yield, m.p. 137° C.

EXAMPLE 12 a. Under the conditions of Example 7(a), 10 g. of the ethyl ester of 3-bromo-2-oxocyclohexanecarboxylic acid is reacted with 2,3-dichloroaniline to the ethyl ester of 7,8-dichloro-1,2,3,4-tetrahydrocarbazole-1-carboxylic acid.

b. The thus-prepared tetrahydrocarbazole derivative is dissolved in o-dichlorobenzene and, after being combined with 10% palladium-carbon, dehydrogenated as set forth in Example 1(b), thus obtaining, after recrystallization from isopropyl alcohol, the ethyl ester of 7,8-dichlorocarbazole-1-carboxylic acid in a 60% yield, m.p. 107° C.

EXAMPLE 13 a. Under the conditions of Example 1(a), 10 g. of the isoamyl ester of 3-bromo-2-oxocyclohexanecarboxylic acid is reacted with 2,3-dichloroaniline to the isoamyl ester of 7,8-dichloro-1,2,3,4-tetrahydrocarbazole-1-carboxylic acid.

b. The tetrahydrocarbazole derivative obtained as described above is dissolved in o-dichlorobenzene, mixed with 10% palladium-carbon, and dehydrogenated as set forth in Example 1(b), thus obtaining, after recrystallization from methanol, the isoamyl ester of 7,8-dichlorocarbazole-1-carboxylic acid in a 45% yield, m.p. 66° C.

EXAMPLE 14 a. Under the conditions of Example 7(a), 10 g. of the ethyl ester of 3-bromo-2-oxocyclohexanecarboxylic acid is reacted with 2,3-dimethylaniline to the ethyl ester of 7,8-dimethyl-1,2,3,4-tetrahydrocarbazole-1-carboxylic acid.

b. The thus-produced tetrahydrocarbazole derivative is dissolved in xylene, mixed with 10% palladium-carbon, and dehydrogenated as set forth in Example 1(b). After recrystallization from isopropyl alcohol, the ethyl ester of 7,8-dimethylcarbazole-1-carboxylic acid is obtained in a 66% yield, m.p. 93° C.

EXAMPLE 15

Under the conditions of Example 9, the ethyl ester of 7,8-dimethyl-1,2,3,4-tetrahydrocarbazole-1-carboxylic acid is dehydrogenated with chloranil; after recrystallization from isopropyl alcohol, the ethyl ester of 7,8-dimethylcarbazole-1-carboxylic acid is obtained in a 50% yield, m.p. 92° C.

EXAMPLE 16

3.1 g. of the ethyl ester of 5-chloro-8-methoxy-1,2,3,4-tetrahydrocarbazole-1-carboxylic acid is refluxed with 20 ml. of xylene and 3 g. of 10% palladium-carbon for 6 hours. The mixture is allowed to cool, the catalyst is filtered off, the solution is concentrated under vacuum, and the residue is recrystallized from ethanol, thus producing 2.0 g. (= 66%) of the ethyl ester of 8-methoxycarbazole-1-carboxylic acid, m.p. 75° C.

EXAMPLE 17

Under the conditions of Example 16, the ethyl ester of 7-chloro-8-methyl-1,2,3,4-tetrahydrocarbazole-1-carboxylic acid is dehydrogenated; after recrystallization from methanol, the ethyl ester of 8-methylcarbazole-1-carboxylic acid is obtained in a 60% yield, m.p. 68° C.

EXAMPLE 18

1.2 g. of the ethyl ester of 6-methoxycarbazole-1-carboxylic acid is mixed with 2 ml. of ethanol and a solution of 2.5 g. of potassium hydroxide in 10 ml. of water and refluxed for 4 hours under agitation. The mixture is then poured into water, filtered, the filtrate acidified by the dropwise addition of hydrochloric acid, the thus-separated crude product is recrystallized from acetone - ethyl acetate, and 0.8 g. of 6-methoxycarbazole-1-carboxylic acid (= 80%) is thus obtained, m.p. 262° C.

EXAMPLE 19

Under the conditions of Example 18, the 8-methoxycarbazole-1-carboxylic acid ethyl ester is saponified; after recrystallization from methanol, 8-methoxycarbazole-1-carboxylic acid is obtained in a 65% yield, m.p. 252° C.

EXAMPLE 20

Under the conditions of Example 18, the 8-methylcarbazole-1-carboxylic acid ethyl ester is saponified. After recrystallization from acetic acid, 8-methylcarbazole-1-carboxylic acid is obtained in a 70% yield, m.p. 286° C.

EXAMPLE 21

Under the conditions of Example 18, the ethyl ester of 7-fluorocarbazole-1-carboxylic acid is saponified, thus obtaining, after recrystallization from dioxane - water, 7-fluorocarbazole-1-carboxylic acid in a 70% yield, m.p. 260° C.

EXAMPLE 22

2.2 g. of the ethyl ester of 7-chloro-8-methylcarbazole-1-carboxylic acid is mixed with a solution of 4.2 g. of potassium hydroxide, 50 ml. of water, and 5 ml. of dimethyl sulfoxide and refluxed for 6 hours. The mixture is then diluted with 50 ml. of hot water, filtered, the filtrate acidified dropwise with hydrochloric acid, the thus-separated filtrate is recrystallized from dioxane - water, and the product is 1.5 g. (= 77%) of 7-chloro-8-methylcarbazole-1-carboxylic acid, m.p. 249° C.

EXAMPLE 23

Under the conditions of Example 22, the ethyl ester of 5-chloro-8-methylcarbazole-1-carboxylic acid is saponified. After recrystallization from dioxane - water, 5-chloro-8-methylcarbazole-1-carboxylic acid is obtained in a 55% yield, m.p. 303° C.

EXAMPLE 24

Under the conditions of Example 22, the ethyl ester of 7-chloro-3,8-dimethylcarbazole-1-carboxylic acid is saponified, thus obtaining after recrystallization from dioxane-water, 7-chloro-3,8-dimethylcarbazole-1-carboxylic acid in an 85% yield, m.p. 294° C.

EXAMPLE 25

Under the conditions set forth in Example 22, the ethyl ester of 5-chloro-8-methoxycarbazole-1-carboxylic acid is saponified. After recrystallization from dioxane, 5-chloro-8-methoxycarbazole-1-carboxylic acid is obtained in a 70% yield, m.p. 328° C.

EXAMPLE 26

Under the conditions of Example 22, the ethyl ester of 7,8-dichlorocarbazole-1-carboxylic acid is saponified. After recrystallization from dioxane - water, 7,8-dichlorocarbazole-1-carboxylic acid is obtained in an 83% yield, m.p. 290° C.

EXAMPLE 27

Under the conditions of Example 22, the ethyl ester of 7,8-dimethylcarbazole-1-carboxylic acid is saponified and, after recrystallization from dioxane, 7,8-dimethylcarbazole-1-carboxylic acid is obtained in a 65% yield, the melting point of this compound being 239° C.

EXAMPLE 28

Under the conditions of Example 22, the ethyl ester of 6-fluorocarbazole-1-carboxylic acid is saponified, yielding 6-fluorocarbazole-1-carboxylic acid, m.p. 254° C. in a 92% yield after recrystallization from dioxane - water.

EXAMPLE 29

Under the conditions of Example 22, the ethyl ester of 7-trifluoromethylcarbazole-1-carboxylic acid is saponified, thus obtaining, after recrystallization from dioxane - water, 7-trifluoromethylcarbazole-1-carboxylic acid in an 83% yield, m.p. 266° C.

EXAMPLE 30 a. A suspension of 0.3 g. of lithium aluminum hydride in 5 ml. of absolute tetrahydrofuran is combined dropwise with 0.560 g. of the ethyl ester of 7-chloro-8-methylcarbazole-1-carboxylic acid, dissolved in 10 ml. of absolute tetrahydrofuran; the mixture is agitated for one hour at room temperature. Then, the reaction mixture is heated for one hour under reflux, allowed to cool, diluted with 20 ml. of ethyl acetate, mixed under cooling dropwise with hydrochloric acid, and the organic phase is separated, washed, and concentrated under vacuum. The residue is recrystallized from toluene, thus obtaining, in a 95% yield, 7-chloro-1-hydroxymethyl-8-methylcarbazole, m.p. 187° C.

b. The thus-obtained hydroxymethyl compound is combined with pyridine and acetic anhydride, allowed to stand for 30 minutes at room temperature, and taken up in chloroform. The chloroform solution is washed, concentrated under vacuum, and the product is 7-chloro-1-acetoxymethyl-8-methylcarbazole in an 85% yield, in the form of a vitrifying mass.

EXAMPLE 31

7.8 g. of 7-chloro-8-methylcarbazole-1-carboxylic acid is combined with 200 ml. of diethyl ether and cooled to −10° C. Under agitation, 8.7 g. of phosphorus pentachloride is introduced into the suspension, and the mixture is stirred for 2 hours at about 0° C. Thereafter, dry ammonia is introduced for one hour under agitation into the reaction mixture, and the latter is stirred for another 10 hours at room temperature.

The reaction mixture is then poured into water, extracted with ethyl acetate, the extract is washed and concentrated, and the residue is recrystallized from dioxane, thus obtaining 7.1 g. (= 91%) of 7-chloro-8-methylcarbazole-1-carboxylic acid amide, m.p. 223° C.

EXAMPLE 32

Under the conditions of Example 31, but with the difference that excess morpholine is added to the reaction mixture in place of the ammonia, 7,8-dimethylcarbazole-1-carboxylic acid is converted into the carboxylic acid morpholide. After recrystallization from dioxane - water, 7,8-dimethylcarbazole-1-carboxylic acid morpholide is obtained in a 75% yield, m.p. 183° C.

EXAMPLE 33 a. Under cooling, a solution of 200 mg. of hydroxylamine in 15 ml. of ethanol is combined with 10 ml. of a sodium ethylate solution containing 1% sodium, as well as, in incremental portions, with 1.0 g. of the ethyl ester of 7-chloro-8-methylcarbazole-1-carboxylic acid. The mixture is stirred for one hour at 0° C. and for another 12 hours at room temperature and is then concentrated under vacuum. The residue is taken up in water, acidified to pH 1 with hydrochloric acid, extracted with ethyl acetate, and the extract is washed and concentrated. The residue is recrystallized from ethanol - water, thus obtaining in a 20% yield, 7-chloro-8-methylcarbazole-1-carbohydroxamic acid, m.p. 200° C.

b. 1.8 g. of 7-chloro-8-methylcarbazole-1-carboxylic acid is introduced into 13 g. of thionyl chloride, mixed with 0.5 ml. of dimethylformamide, and agitated for one hour at room temperature. The mixture is then combined with 10 ml. of absolute chloroform, heated for two hours to 60° C., and concentrated under vacuum. To remove the thionyl chloride, the residue is taken up repeatedly in chloroform, and the thus-obtained solution is concentrated under vacuum. The crude product is recrystallized from petroleum ether - chloroform, resulting in 7-chloro-8-methylcarbazole-1-carboxylic acid chloride, m.p. 130° C.

The thus-produced acid chloride is combined with 15 ml. of ether and 1.3 g. of crystalline hydroxylamine and stirred for 16 hours at room temperature. The precipitate is then vacuum-filtered, washed with ether, and dissolved in water. The aqueous solution is acidified to pH 1 with 2N hydrochloric acid, extracted with ethyl acetate, and the extract is concentrated. The residue is recrystallized from dioxane - water, thus obtaining 0.72 g. (= 40%) of 7-chloro-8-methylcarbazole-1-carbohydroxamic acid, m.p. 200° C.

EXAMPLE 34 a. Under the conditions of Example 7(a), 10 g. of the ethyl ester of 3-bromo-2-oxocyclohexanecarboxylic acid is reacted with 3-chloro-4-methylaniline to obtain the ethyl ester of 7-chloro-6-methyl-1,2,3,4-tetrahydrocarbazole-1-carboxylic acid and the ethyl ester of 5-chloro-6-methyl-1,2,3,4-tetrahydrocarbazole-1-carboxylic acid, which are separated by chromatography.

b. The thus-produced 7-chloro-6-methyltetrahydrocarbazole derivative is dissolved in chlorobenzene, mixed with 10% palladium-carbon, and dehydrogenated as set forth in Example 1(b), thus obtaining, after recrystallization from isopropyl alcohol, the ethyl ester of 7-chloro-6-methylcarbazole-1-carboxylic acid in a 75% yield, m.p. 155° C.

EXAMPLE 35

Under the conditions of Example 18, the ethyl ester of 7-chloro-6-methylcarbazole-1-carboxylic acid is saponified. After recrystallization from ethanol - dioxane, 7-chloro-6-methylcarbazole-1-carboxylic acid is obtained in an 85% yield, m.p. 310° C.

EXAMPLE 36

The 5-chlorotetrahydrocarbazole derivative produced in accordance with Example 33(a) is dissolved in chlorobenzene, mixed with 10% palladium-carbon, and dehydrogenated as described in Example 1(b). After recrystallization from isopropyl alcohol, the ethyl ester of 5-chloro-6-methylcarbazole-1-carboxylic acid is obtained in an 80% yield, m.p. 160° C.

EXAMPLE 37

Under the conditions of Example 18, the ethyl ester of 5-chloro-6-methylcarbazole-1-carboxylic acid is saponified. After recrystallization from dioxane - water, 5-chloro-6-methylcarbazole-1-carboxylic acid is obtained in a 70% yield, m.p. 305° C.

EXAMPLE 38 a. Under the conditions of Example 7(a), 10 g. of the ethyl ester of 3-bromo-2-oxocyclohexanecarboxylic acid is reacted with 2-chloro-3-methylaniline to the ethyl ester of 8-chloro-7-methyl-1,2,3,4-tetrahydrocarbazole-1-carboxylic acid.

b. The thus-produced tetrahydrocarbazole derivative is dissolved in chlorobenzene, mixed with 10% palladium-carbon and dehydrogenated as described in Example 1(b), thus obtaining after recrystallization from isopropyl alcohol, in a 60% yield, the ethyl ester of 8-chloro-7-methylcarbazole-1-carboxylic acid, m.p. 73° C.

EXAMPLE 39

Under the conditions of Example 18, the ethyl ester of 8-chloro-7-methylcarbazole-1-carboxylic acid is saponified. After recrystallization from dioxane, 8-chloro-7-methylcarbazole-1-carboxylic acid is obtained in a 75% yield, m.p. 266° C.

EXAMPLE 40 a. Under the conditions of Example 7(a), 10 g. of the ethyl ester of 3-bromo-2-oxocyclohexanecarboxylic acid is reacted with 3-chloro-2-ethylaniline to the ethyl ester of 7-chloro-8-ethyl-1,2,3,4-tetrahydrocarbazole-1-carboxylic acid.

b. The thus-produced tetrahydrocarbazole derivative is dissolved in chlorobenzene and, after being combined with 10% palladium-carbon, dehydrogenated as described in Example 1(b). Yield: the ethyl ester of 7-chloro-8-ethylcarbazole-1-carboxylic acid.

EXAMPLE 41

Under the conditions of Example 18, the ethyl ester of 7-chloro-8-ethylcarbazole-1-carboxylic acid is saponified, thus obtaining 7-chloro-8-ethylcarbazole-1-carboxylic acid.

EXAMPLE 42 a. Under the conditions of Example 7(a), 10 g. of the ethyl ester of 3-bromo-2-oxocyclohexanecarboxylic acid is reacted with α-naphthylamine to the ethyl ester of benzo[a]1,2,3,4-tetrahydrocarbazole-1-carboxylic acid.

b. The thus-produced tetrahydrocarbazole derivative is dissolved in xylene, mixed with 10% palladium-carbon, and dehydrogenated as set forth in Example 1(b); recrystallization from isopropyl alcohol yields, in a 70% quantity, the ethyl ester of benzo[a]carbazole-1-carboxylic acid, m.p. 93° C.

EXAMPLE 43

Under the conditions of Example 18, the ethyl ester of benzo[a]carbazole-1-carboxylic acid is saponified. After recrystallization from methanol - dioxane, benzo[a]carbazole-1-carboxylic acid is obtained in an 80% yield, m.p. 343° C.

EXAMPLE 44

1.3 g. of 7,8-dichlorocarbazole-1-carboxylic acid is dissolved in 30 ml. of absolute dimethyl glycol and combined with 0.6 g. of triethylamine. The mixture is cooled to −10° C., mixed with 0.63 g. of isobutyl chloroformate, and agitated for 20 minutes at −10° C. The thus-produced precipitate is rapidly vacuumfiltered, the filtrate is combined with 0.5 g. of dimethylaminoethanol in 2 ml. of dimethyl glycol, agitated for 10 minutes at −10° C, and allowed to stand for about 16 hours at approximately 0° C.

The reaction mixture is then concentrated under vacuum, the residue is taken up in ether, filtered, and the filtrate is washed, dried, and concentrated under vacuum, thus obtaining 1.6 g. (= 99%) of the (2'-dimethylaminoethyl) ester of 7,8-dichlorocarbazole-1-carboxylic acid in the form of an oil.

EXAMPLE 45

Under the conditions of Example 31, but adding 2-dimethylaminoethanol in place of the ammonia, the (2'-dimethylaminoethyl) ester of 7-chloro-8-methylcarbazole-1-carboxylic acid, m.p. 91° C. (from cyclohexane) is obtained.

EXAMPLE 46

1.0 g. of the ethyl ester of 7-chloro-8-methylcarbazole-1-carboxylic acid in 20 ml. of dimethylformamide is combined with 0.2 g. of approximately 50% sodium hydride suspension and agitated for 4 hours at room temperature. Then, the mixture is combined with 0.8 g. of methyl iodide and agitated for another 12 hours. The solvent is distilled off under vacuum, the residue is taken up in chloroform, and the chloroform phase is washed and concentrated. The residue is purified by means of cyclohexane - toluene over a silica gel column, thus obtaining 0.74 g. (= 70%) of the ethyl ester of 7-chloro-8,9-dimethylcarbazole-1-carboxylic acid as an oil.

EXAMPLE 47

Under the conditions of Example 18, the ethyl ester of 7-chloro-8,9-dimethylcarbazole-1-carboxylic acid is saponified. After recrystallization from dioxane - water, 7-chloro-8,9-dimethylcarbazole-1-carboxylic acid is obtained in a 75% yield, m.p. 237° C.

EXAMPLE 48

Under the conditions of Example 46, but using benzyl chloride in place of methyl iodide, the ethyl ester of 7-chloro-8-methylcarbazole-1-carboxylic acid is converted, in a 65% yield, into the ethyl ester of 7-chloro-8-methyl-9-benzylcarbazole-1-carboxylic acid, m.p. 81° C. (from methanol).

EXAMPLE 49

Under the conditions of Example 18, the ethyl ester of 7-chloro-8-methyl-9-benzylcarbazole-1-carboxylic acid is saponified, thus obtaining after recrystallization from methanol, in a 75% yield, 7-chloro-8-methyl-9-benzylcarbazole-1-carboxylic acid, m.p. 190° C.

EXAMPLE 50

Under agitation, 3.9 g. of 7-chloro-8-methylcarbazole-1-carboxylic acid amide is introduced in incremental portions into 15 ml. of phosphorus oxychloride. The mixture is then gradually heated to 120° C. and maintained at this temperature for 2 hours. The reaction mixture is then allowed to cool and poured, under vigorous agitation, into a solution of 100 ml. of ice water and 25 ml. of aqueous ammonia solution. The thus-formed precipitate is vacuum-filtered and recrystallized from isopropyl alcohol, thus producing 2.7 g. (= 75%) of 7-chloro-8-methylcarbazole-1-carbonitrile, m.p. 267° C.

EXAMPLE 51

2.1 g. of 7-chloro-8-methylcarbazole-1-carbonitrile is dissolved in 50 ml. of hexamethylphosphoric triamide and combined with 5.2 g. of sodium azide under agitation. The mixture is stirred for 20 minutes and then, under cooling, 6.1 ml. of 98% formic acid is added dropwise thereto. The reaction mixture is then agitated for 3 days at 60°–70° C., whereupon it is poured into a mixture of 50 g. of ice and 200 ml. of 0.5N sodium hydroxide solution. Additional amounts of sodium hydroxide solution are added until a pH of 10 has been reached.

The mixture is extracted with chloroform, the chloroform phase is discarded, and the aqueous phase is acidified to pH 3 with hydrochloric acid and extracted with ether. The ether phase is dried and concentrated, and the residue is recrystallized from isopropyl alcohol, thus obtaining 2.5 g. (= 98%) of 7-chloro-8-methyl-1-(5-tetrazolyl)-carbazole, m.p. 279° C.

EXAMPLE 52 a. 4-Chloro-5,6,7,8-tetrahydrocarbazole-1-carboxylic acid is combined with methanol containing hydrogen chloride and stored for 16 hours at room temperature. The mixture is then diluted with methanol, the solution is neutralized by shaking with "Amberlite IR 4B," concentrated under vacuum, and the residue is recrystallized from isopropyl alcohol, thus producing the methyl ester of 4-chloro-5,6,7,8-tetrahydrocarbazole-1-carboxylic acid.

b. The thus-prepared tetrahydrocarbazole derivative is dissolved in chlorobenzene, combined with 10% palladium-carbon, and dehydrogenated as set forth in Example 1(b), thus obtaining after recrystallization from isopropyl alcohol, in a 65% yield, the methyl ester of 4-chlorocarbazole-1-carboxylic acid, m.p. 136° C.

EXAMPLE 53

Under the conditions of Example 18, the methyl ester of 4-chlorocarbazole-1-carboxylic acid is saponified. After recrystallization from isopropyl alcohol, 4-chlorocarbazole-1-carboxylic acid is obtained in a 70% yield, m.p. 280° C.

EXAMPLE 54 a. Under the conditions of Example 1(a), 10 g. of the methyl ester of 5-chloroanthranilic acid is reacted with 2-bromocyclohexanone to the methyl ester of 3-chloro-5,6,7,8-tetrahydrocarbazole-1-carboxylic acid.

b. The thus-produced tetrahydrocarbazole derivative is dissolved in chlorobenzene, combined with 10% palladium-carbon, and dehydrogenated as described in Example 1(b), thus obtaining after recrystallization from isopropyl alcohol, in a 65% yield, the methyl ester of 3-chlorocarbazole-1-carboxylic acid, m.p. 169° C.

EXAMPLE 55

Under the conditions of Example 18, the methyl ester of 3-chlorocarbazole-1-carboxylic acid is saponified, thus obtaining, after recrystallization from ethyl acetate, in an 85% yield 3-chlorocarbazole-1-carboxylic acid, m.p. 245° C.

EXAMPLE 56 a. Under the conditions of Example 7(a), 10 g. of the methyl ester of 4-methylanthranilic acid is reacted with 2-bromocyclohexanone to the methyl ester of 4-methyl-5,6,7,8-tetrahydrocarbazole-1-carboxylic acid.

b. The thus-produced tetrahydrocarbazole derivative is dissolved in xylene, combined with 10% palladium-carbon, dehydrogenated as described in Example 1(b), and the methyl ester of 4-methylcarbazole-1-carboxylic acid is thus obtained.

EXAMPLE 57

Under the conditions of Example 18, the 4-methylcarbazole-1-carboxylic acid methyl ester is saponified, yielding 4-methylcarbazole-1-carboxylic acid.

EXAMPLE 58 a. Under the conditions of Example 1(a), 10 g. of the methyl ester of 5-methylanthranilic acid is reacted with 2-bromocyclohexanone to the methyl ester of 3-methyl-5,6,7,8-tetrahydrocarbazole-1-carboxylic acid.

b. The thus-produced tetrahydrocarbazole derivative is dissolved in xylene, mixed with 10% palladium-carbon, dehydrogenated as set forth in Example 1(b), and the product is the methyl ester of 3-methylcarbazole-1-carboxylic acid.

EXAMPLE 59

Under the conditions of Example 18, the methyl ester of 3-methylcarbazole-1-carboxylic acid is saponified, yielding 3-methylcarbazole-1-carboxylic acid.

EXAMPLE 60

15.7 g. of the methyl ester of 2-amino-5-chlorobenzoic acid is combined with 0.5 g. of zinc chloride and 7.1 g. of 2-bromocyclohexanone and heated for 5 hours to 160° C.

The mixture is then allowed to cool, diluted with toluene, the toluene phase washed with dilute hydrochloric acid and water, dried, and concentrated under vacuum.

The remainder is recrystallized from isopropyl alcohol-cyclohexanone, thus obtaining 4.5 g. (= 42%) of the methyl ester of 3-chloro-5,6,7,8-tetrahydrocarbazole-1-carboxylic acid.

EXAMPLE 61

1.2 g. of the methyl ester of 3-chloro-5,6,7,8-tetrahydrocarbazole-1-carboxylic acid is agitated for 10 minutes in a mixture of 15 ml. of isopropyl alcohol and 35% aqueous sodium hydroxide solution in a bath having a temperature of 110° C. The isopropyl alcohol is then gradually distilled off, the sodium salt of 3-chloro-5,6,7,8-tetrahydrocarbazole-1-carboxylic acid is filtered off, washed with ether, and dried. The salt is taken up in dilute hydrochloric acid and extracted with ethyl acetate. The extract is concentrated, the residue is recrystallized from ethyl acetate, thus obtaining 0.9 g. (= 80%) of 3-chloro-5,6,7,8-tetrahydrocarbazole-1-carboxylic acid, m.p. 251° C.

EXAMPLE 62

Under the conditions of Example 60, 2-bromocyclohexanone is reacted with the methyl ester of 2-amino-5-methylbenzoic acid; after recrystallization from cyclohexane, the methyl ester of 3-methyl-5,6,7,8-tetrahydrocarbazole-1-carboxylic acid is obtained in a 55% yield, m.p. 111° C.

EXAMPLE 63

Under the conditions of Example 61, the methyl ester of 3-methyl-5,6,7,8-tetrahydrocarbazole-1-carboxylic acid is saponified. After recrystallization from isopropyl alcohol, 3-methyl-5,6,7,8-tetrahydrocarbazole-1-carboxylic acid is obtained in a 75% yield, m.p. 225° C.

EXAMPLE 64 a. Under the conditions of Example 59, 2-bromocyclohexanone is reacted with the methyl ester of N-methylanthranilic acid. After recrystallization from methanol, the methyl ester of 9-methyl-5,6,7,8-tetrahydrocarbazole-1-carboxylic acid is obtained in a 15% yield, m.p. 56° C.

b. Under the conditions of Example 46, the 5,6,7,8-tetrahydrocarbazole-1-carboxylic acid methyl ester is methylated, thus obtaining in a 65% yield the methyl ester of 9-methyl-5,6,7,8-tetrahydrocarbazole-1-carboxylic acid.

EXAMPLE 65

Under the conditions of Example 61, the methyl ester of 9-methyl-5,6,7,8-tetrahydrocarbazole-1-carboxylic acid is saponified and, after recrystallization from ethanol, 9-methyl-5,6,7,8-tetrahydrocarbazole-1-carboxylic acid is obtained in a 75% yield, m.p. 180° C.

EXAMPLE 66

| | Composition for an Ointment: |
|---|---|
| 0.05 % | Ethyl ester of 7-chloro-8-methylcarbazole-1-carboxylic acid |
| 2.50 % | "Allercur" hexachlorophenate, micronized, particle size about 8 μ ("Allercur" = registered trademark for 1-p-chlorobenzyl-2-pyrrolidylmethylbenzimidazole) |
| 6.00 % | "Hostaphat KW 340" (tertiary ester of o-phosphoric acid and wax alcohol tetraglycol ether) |
| 0.10 % | Sorbic acid |
| 10.00 % | Neutral oil ("Migloyol 812") |
| 3.50 % | Stearyl alcohol |
| 1.50 % | Lanolin, anhydrous DAB [German Pharmacopoeia] 6 |
| 76.35 % | Desalted water |

EXAMPLE 67

| | Composition for an Ointment: |
|---|---|
| 0.05 g. | Ethyl ester of 8-chloro-7-methylcarbazole-1-carboxylic acid |
| 5.00 g. | White wax, DAB 6 |
| 5.00 g. | Lanolin, anhydrous DAB 6 |
| 20.00 g. | Vaseline, white DAB 6 |
| 25.00 g. | Amphocerin K "Dehydag" |
| 14.95 g. | Paraffin oil, liquid DAB 6 |
| 30.00 g. | Water, desalted |
| 0.02 g. | "Crematest" perfume oil No. 6580 "Dragee" |

EXAMPLE 68

1.000 g. of micronized ethyl ester of 7-chloro-8-methylcarbazole-1-carboxylic acid (average particle size: smaller than 7 μ) and 39.000 g. of ground lactose are mixed together; respectively 40 mg. of the mixture are filled into mating capsules. The inhalant can be administered, after opening the capsule, by inhaling, preferably by sniffing, or a "Spinhaler" is utilized for the application of the inhalant.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A carbazole of the formula

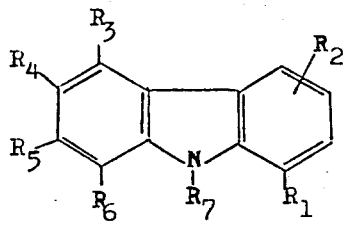

wherein $R_1$ is a hydroxymethyl group, alkanoyloxymethyl of 1–8 carbon atoms in the alkanoyl group, tetrazolyl, cyano, oximinocarbonyl, aminocarbonyl, alkoxycarbonyl, dialkylaminoalkoxycarbonyl, dialkylaminocarbonyl, wherein alkoxy is of 1–8 carbon atoms and alkyl is of 1–4 carbon atoms, N-morpholinocarbonyl, or carboxy or a salt thereof with a physiologically acceptable base, 1 or 2 of $R_2$ through $R_6$ is a halogen atom, and the remainder are hydrogen atoms, alkyl of 1–4 carbon atoms, trifluoromethyl, or alkoxy of 1–4 carbon atoms, or $R_5$ and $R_6$ collectively with the carbon atoms to which they are attached also are a cyclopentene, cyclohexene or benzene ring, and $R_7$ is a hydrocarbon of 3–8 carbon atoms, or a hydrogen atom.

2. A compound of claim 1 wherein $R_1$ is carboxy.

3. A compound of claim 2 wherein $R_2$, $R_3$ and $R_4$ each are hydrogen atoms and $R_5$ and $R_6$ are other than a hydrogen atom.

4. 1-ethoxycarbonyl-6-methoxycarbazole.

5. 1-ethoxycarbonyl-8-methoxycarbazole.

6. A compound of claim 1, 1-ethoxycarbonyl-7-fluorocarbazole.

7. A compound of claim 1, 1-ethoxycarbonyl-6-fluorocarbazole.

8. 1-ethoxycarbonyl-7-trifluoromethylcarbazole.

9. A compound of claim 1, 1-ethoxycarbonyl-5-chloro-8-methylcarbazole.

10. A compound of claim 1, 1-ethoxycarbonyl-7-chloro-8-methylcarbazole.

11. A compound of claim 1, 1-ethoxycarbonyl-5-chloro-8-methoxycarbazole.

12. A compound of claim 1, 1-ethoxycarbonyl-7-chloro-3,8-dimethylcarbazole.

13. A compound of claim 1, 1-ethoxycarbonyl-7,8-dichlorocarbazole.

14. A compound of claim 1, 1-isoamyloxycarbonyl-7,8-dichlorocarbazole.

15. A compound of claim 1, 7-fluorocarbazole-1-carboxylic acid.

16. A compound of claim 1, 7-chloro-8-methylcarbazole-1-carboxylic acid.

17. A compound of claim 1, 5-chloro-8-methylcarbazole-1-carboxylic acid.

18. A compound of claim 1, 7-chloro-3,8-dimethylcarbazole-1-carboxylic acid.

19. A compound of claim 1, 5-chloro-8-methoxycarbazole-1-carboxylic acid.

20. A compound of claim 1, 7,8-dichlorocarbazole-1-carboxylic acid.

21. A compound of claim 1, 6-fluorocarbazole-1-carboxylic acid.

22. 7-trifluoromethylcarbazole-1-carboxylic acid.

23. A compound of claim 1, 7-chloro-1-hydroxymethyl-8-methylcarbazole.

24. A compound of claim 1, 7-chloro-8-methylcarbazole-1-carboxylic acid amide.

25. 7,8-dimethylcarbazole-1-carboxylic acid morpholide.

26. A compound of claim 1, 7-chloro-8-methylcarbazole-1-carbohydroxamic acid.

27. A compound of claim 1, 1-ethoxycarbonyl-7-chloro-6-methylcarbazole.

28. A compound of claim 1, 7-chloro-6-methylcarbazole-1-carboxylic acid.

29. A compound of claim 1, 1-ethoxycarbonyl-5-chloro-6-methylcarbazole.

30. A compound of claim 1, 5-chloro-6-methylcarbazole-1-carboxylic acid.

31. A compound of claim 1, 1-ethoxycarbonyl-8-chloro-7-methylcarbazole.

32. A compound of claim 1, 8-chloro-7-methylcarbazole-1-carboxylic acid.

33. A compound of claim 1, 1-ethoxycarbonyl-7-chloro-8-ethylcarbazole.

34. A compound of claim 1, 7-chloro-8-ethylcarbazole-1-carboxylic acid.

35. A compound of claim 1, 1-methoxycarbonyl-4-chlorocarbazole.

36. A compound of claim 1, 4-chlorocarbazole-1-carboxylic acid.

37. A compound of claim 1, 1-methoxycarbonyl-3-chlorocarbazole.

38. A compound of claim 1, 3-chlorocarbazole-1-carboxylic acid.

39. A compound of claim 1, 1-ethoxycarbonyl-benzo[a]carbazole.

40. A compound of claim 1, benzo[a]carbazole-1-carboxylic acid.

41. A compound of claim 1, the (2'-dimethylaminoethyl) ester of 7,8-dichlorocarbazole-1-carboxylic acid.

42. A compound of claim 1, the (2'-dimethylaminoethyl) ester of 7-chloro-8-methylcarbazole-1-carboxylic acid.

43. A compound of claim 1, 1-ethoxycarbonyl-7-chloro-8,9-dimethylcarbazole.

44. A compound of claim 1, 7-chloro-8,9-dimethylcarbazole-1-carboxylic acid.

45. A compound of claim 1, 1-ethoxycarbonyl-7-chloro-8-methyl-9-benzylcarbazole.

46. A compound of claim 1, 7-chloro-8-methyl-9-benzylcarbazole-1-carboxylic acid.

47. A compound of claim 1, 7-chloro-8-methylcarbazole-1-carbonitrile.

48. A compound of claim 1, 7-chloro-8-methyl-1-(5-tetrazolyl)-carbazole.

49. A compound of claim 1, 7-chloro-1-acetoxymethyl-8-methylcarbazole.

\* \* \* \* \*